US 6,595,213 B2

(12) United States Patent
Bennarsten

(10) Patent No.: US 6,595,213 B2
(45) Date of Patent: Jul. 22, 2003

(54) HIGH-FREQUENCY OSCILLATOR VENTILATOR

(75) Inventor: Johan Bennarsten, Gustavsberg (SE)

(73) Assignee: Siemens Elema AB, Solna (SE)

( * ) Notice: Subject to any disclaimer, the term of this patent is extended or adjusted under 35 U.S.C. 154(b) by 8 days.

(21) Appl. No.: 09/767,221

(22) Filed: Jan. 23, 2001

(65) Prior Publication Data

US 2001/0009152 A1 Jul. 26, 2001

(30) Foreign Application Priority Data

Jan. 25, 2000 (SE) .............................................. 0000206

(51) Int. Cl.⁷ .............................. A62B 7/00; A62B 9/00
(52) U.S. Cl. ............................. 128/205.19; 128/204.18; 128/204.21
(58) Field of Search ..................... 128/204.18, 204.21, 128/204.28, 205.14, 205.19

(56) References Cited

U.S. PATENT DOCUMENTS

| | | | | |
|---|---|---|---|---|
| 2,918,917 A | * | 12/1959 | Emerson ................ | 128/205.24 |
| 4,127,121 A | * | 11/1978 | Westenskow et al. .. | 128/203.12 |
| 4,463,756 A | * | 8/1984 | Thuc ..................... | 128/204.21 |
| 4,543,951 A | * | 10/1985 | Phuc ..................... | 128/204.25 |
| 4,702,241 A | * | 10/1987 | Gravenstein et al. .. | 128/204.25 |
| 4,747,402 A | | 5/1988 | Reese et al. | |
| 4,770,165 A | * | 9/1988 | Hayek .................... | 128/205.18 |
| 4,821,709 A | * | 4/1989 | Jensen ................... | 128/204.21 |
| 4,989,597 A | * | 2/1991 | Werner .................. | 128/203.12 |
| 5,092,326 A | | 3/1992 | Winn et al. | |
| 5,150,291 A | * | 9/1992 | Cummings et al. .... | 364/413.03 |
| 5,484,427 A | * | 1/1996 | Gibbons ................. | 604/313 |
| 5,507,282 A | * | 4/1996 | Younes .................. | 128/204.21 |
| 5,697,920 A | * | 12/1997 | Gibbons ................. | 604/289 |
| 5,871,008 A | * | 2/1999 | Poon et al. ............. | 128/202.12 |

* cited by examiner

Primary Examiner—Weilun Lo
Assistant Examiner—Joseph F. Weiss
(74) Attorney, Agent, or Firm—Schiff Hardin & Waite

(57) ABSTRACT

A high-frequency oscillator (HFO) ventilator has a gas conduit with an opening for gas connection with a patient's airways and a bias gas flow inlet and outlet disposed to define therebetween a bias gas flow-path within the conduit. An oscillator is operable to induce pressure oscillations in gas within the conduit to move a volume of gas ("tidal volume") along a respiration flow-path, intersecting the bias gas flow-path, alternately in to and out of the opening at a predetermined high-frequency to provide, respectively, an inspiration phase and an expiration phase of a breathing cycle. The HFO ventilator further has an extraction device operable during the breathing cycle, and preferably in timed relation with the operation of the oscillator, to withdraw an additional amount of gas from the respiration flow-path.

7 Claims, 3 Drawing Sheets

HIGH-FREQUENCY OSCILLATOR VENTILATOR

BACKGROUND OF THE INVENTION

1. Field of the Invention

The present invention relates to a high-frequency oscillator (HFO) ventilator.

2. Description of the Prior Art

An HFO ventilator operates to fully ventilate a patient by introducing pressure oscillations to a column of gas which is in communication with a patient's airways. These oscillations cause the supply of breathing gas to and the active extraction of the supplied volume of gas from the airways of the patient in alternation. The peak-to-peak pressure amplitude about a mean airway pressure is typically between 0.05 and 0.2 bar and oscillates at a typical frequency of between 10 Hz and 50 Hz to supply a tidal volume significantly less than that required during spontaneous breathing, typically at or around anatomical dead-space volumes, and is usually less than that typically supplied by a jet device during HFJ ventilation.

This is also in marked contrast to the operation of conventional mechanical ventilators. Generally, a conventional mechanical ventilator operates to fully ventilate a patient by supplying breathing gas to the patient's airways in an amount and at a frequency substantially equal to those of a spontaneously breathing patient. Typically then, for an adult, a conventional mechanical ventilator will provide a tidal volume of around 500 milliliters at a frequency of around 0.2 Hz.

An HFO ventilator generally has a gas conduit having an opening at one end for connection to the patient's airways and an opposite end in gaseous communication with an oscillator. The oscillator typically includes a reciprocally movable element, such as a membrane or a piston, as part of a variable gas holding volume to which the end of the conduit is in gaseous communication. A drive unit is provided to reciprocate the movable element at a predetermined high-frequency to alternately remove a volume of gas from and return it to the gas conduit. Alternating under-and over-pressure pulses are thereby supplied to gas within the conduit at that frequency and travel along a respiration flow-path which connects the variable gas holding volume to the patient's airways. This causes a column of gas, the volume of which is dependent on the volume change of the oscillator, to be moved out of and in to the patient's airways and thereby provide ventilation. A continuous so called 'bias' flow of fresh breathing gas moves between an inlet and an outlet, along a flow path which intersects the respiration flow-path of the moving column of gas within the conduit. This bias flow washes carbon dioxide ($CO_2$) rich gas, that has been drawn from the patient's lungs by the under-pressure pulse, away from the respiration flow-path. The bias flow also maintains a mean positive airway pressure (or bias) about which pressure the high-frequency pressure pulses oscillate.

In an attempt to ensure adequate $CO_2$ removal a typical bias flow of between 20 to 90 liters per minute, depending largely on whether a child or an adult is being ventilated, is employed. With this highest flow of around 90 liters per minute the $CO_2$ elimination has proven inadequate for adults. Even with children the oscillating frequency has to be reduced so as to enable sufficient $CO_2$ elimination (a reduction in oscillating frequency permits larger tidal volumes to be delivered and removed). However, the operation of the ventilator at less than the optimal physiological frequency often requires the delivered tidal volume to be increased to allow for a sufficient oxygen uptake by the patient, leading to a necessarily lower oscillating frequency, and an increase in bias flow rate.

SUMMARY OF THE INVENTION

It is an object of the present invention to provide a high-frequency oscillator ventilator wherein the aforementioned problems associated with known ventilators of this type are avoided, or are at least alleviated.

This object is achieved by the present invention wherein a high-frequency oscillator ventilator as generally described above is provided with an extraction device, such as a vacuum pump or a variable volume container, to remove from the respiration flow path an amount of $CO_2$ rich breathing gas in addition to that removed by the bias flow, so as to reduce the amount of $CO_2$ re-breathed by the patient.

Preferably, the extraction device is couplable in gaseous communication to the respiration flow-path at a location between the bias-gas flow path and a patient's airways. This has the advantage that $CO_2$ rich gas that would not be washed out with the bias flow and thus which would otherwise be re-breathed is removed from the system to be replaced by fresh gas from the bias gas flow.

The extraction device is operated in timed relationship with the oscillator to withdraw gas only during a part of the breathing cycle which predominantly comprises the expiration phase, and especially an end portion of the expiration phase, when the extracted gas may be analyzed to provide information, for example about end-tidal $CO_2$ levels, useful in monitoring the efficacy of the HFO treatment. By timing the operation of the extraction device to be substantially within the expiration phase, the tidal volume delivered to the patient during the inspiration phase of the oscillator is substantially unaffected by the operation of the extraction device. A flow controller, such as a pressure regulator, is also provided in gas communication with the bias gas flow inlet to vary the flow of bias gas therethrough to compensate for the amount of gas removed by the periodic operation of the extraction device.

DESCRIPTION OF THE PREFERRED EMBODIMENTS

Figure 1:
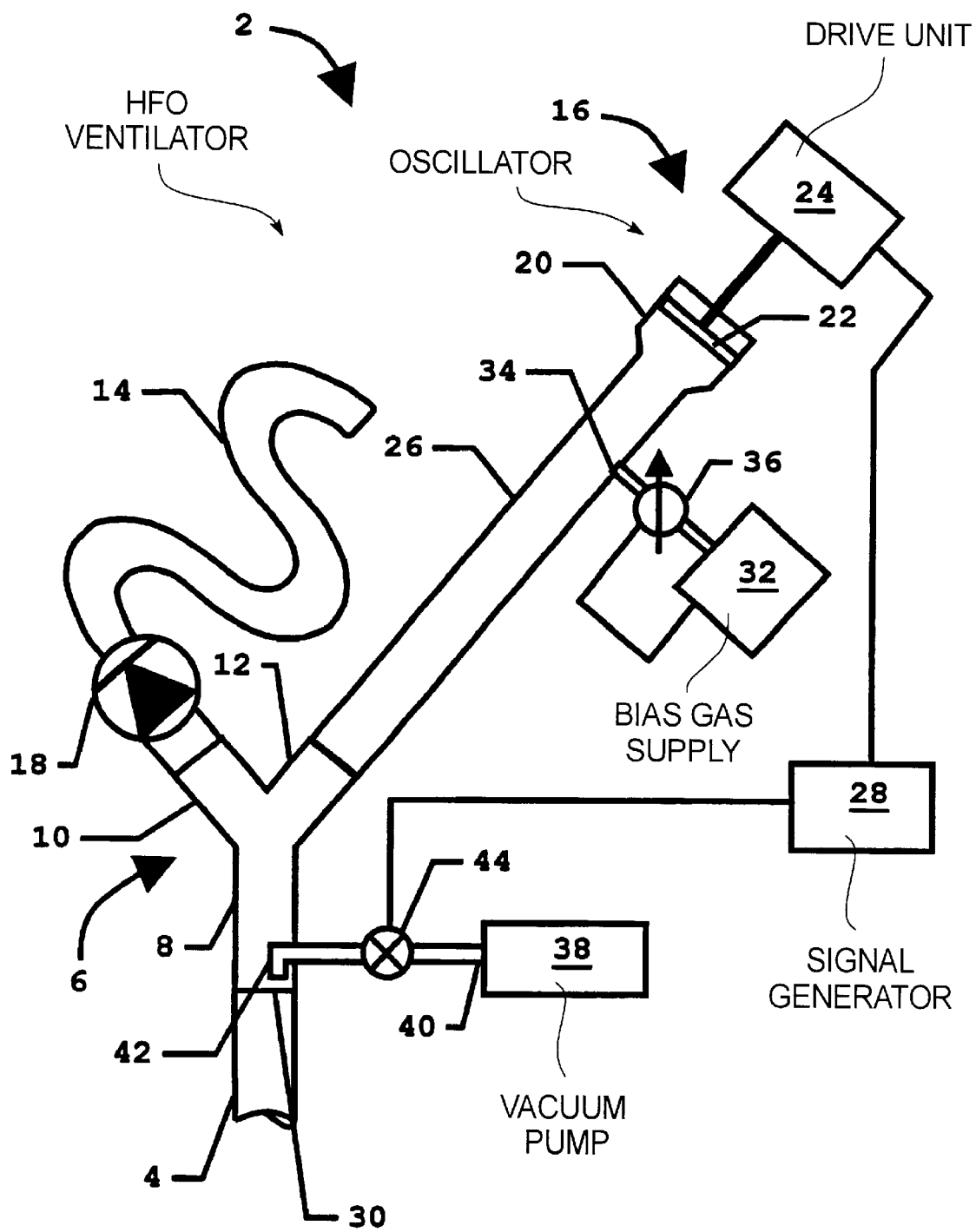
FIG. 1 is a schematic representation of an embodiment of an HFO ventilator according to the present invention.

As shown in FIG. 1, an HFO ventilator 2 is connected to a conventional endotracheal tube 4 which, in use, is intended to be inserted into a patient's airways. A Y-piece 6 of the ventilator 2 is arranged with a common limb 8 connectable to the endotracheal tube 4 and with independent limbs 10, 12 respectively connected to an expiration line 14 and an oscillator 16.

The expiration line 14 is arranged as a low pass filter to provide an increased resistance to gas flowing at operating frequencies of the oscillator unit 16 and is connected to the limb 10 via a pressure regulating valve, such as a one-way valve 18 or a bi-directional valve, which is arranged to allow flow of gas from the Y-piece 6 into the line 14 to maintain the pressure at the patient's airways ("mean airway pressure") at a predetermined level selected to maintain the airways open.

The oscillator 16 in this embodiment has a housing 20 in which a piston head 22 is located but may be any oscillator used in conventional HFO ventilators. The head 22 is reciprocally movable by a drive unit 24 and is arranged in gaseous communication with a conduit 26 which, in turn, is connected to the limb 12 of the Y-piece 6. A signal generator 28 is operably connected to the drive unit 24 of the oscillator 16 to supply a variable frequency control signal of typically between 10 Hz and 50 Hz to the unit 24 which operates to reciprocate the piston head 22 at that supplied frequency. Cyclic pressure oscillations thus induced within gas in the conduit 26 are transmitted along a respiration flow-path connecting the oscillator 16 with a patient's airways and which includes the conduit 26 as well as the limbs 12 and 8 of the Y-piece 6. These pressure oscillations cause a column of gas to move through an opening 30 of the Y-piece 6 into and out of the patient's airways at the frequency of reciprocation of the piston 22 to provide, respectively, inspiration and expiration phases of a patient breathing cycle.

A bias gas supply 32 is connected to the conduit 26 at an inlet 34 via a pressure control valve 36, such as a mushroom valve, which is adapted to vary its opening dependent on a pressure difference on opposite sides of the valve 36. The valve 36 thus regulates the flow of bias gas between the inlet 34 and an outlet 10 to maintain a predetermined pressure within the conduit 26.

A vacuum pump 38 provides a continuous and user-variable vacuum at an input 40 which may be communicated to small bore tube 42 within the common limb 8 of the Y-piece 6 via a controllable on/off valve 44, which operates in a timed relationship with the operation of the oscillator 16. The valve 44 is operably connected to the signal generator 28 to receive a signal synchronously with that signal supplied to the drive unit 24 and is employed to control the operation of the valve 44. In the present example the valve 44 may be controlled by the received signal to open during low pressure phases (corresponding to expiration phases of patient breathing cycles) induced within gas in the conduit 26 as the piston moves to increase the gas holding volume of the housing 20. In this manner breathing gas is extracted from a location proximal the opening 30 during the expiration phases. This causes the pressure within the conduit 26 to drop, the flow control valve 36 to open further and a commensurate increase in bias gas flow to occur.

It will be understood by those skilled in the art that the on/off valve 44 can be operated to open at any point during the breathing cycle or indeed may even be omitted to provide continuous extraction without departing from the invention.

Figure 2:
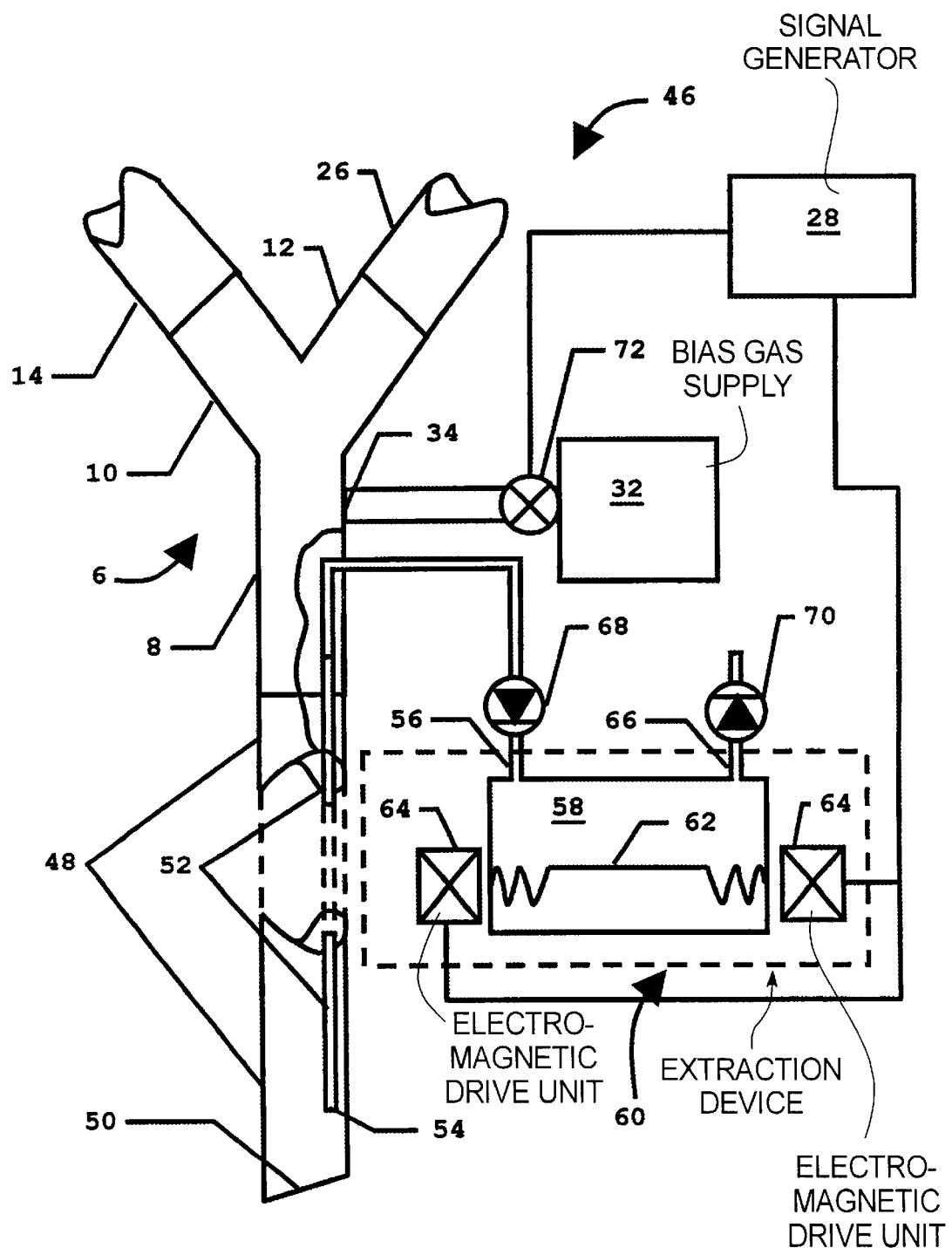
FIG. 2 is a schematic representation of a portion of an alternative embodiment of an HFO ventilator according to the present invention.

A portion of an HFO ventilator 46 is shown in FIG. 2, wherein elements common to the HFO ventilator 2 of FIG. 1 are given identical reference numerals. As described above with respect to the HFO ventilator 2 of FIG. 1, a Y-piece 6 of the HFO ventilator 46 has limbs 10, 12 individually connected to, respectively, an expiration line 14, via a one-way valve 18, and a conduit 26 which provides for gas communication with an oscillator 16 (not shown). The common limb 8 of the Y-piece 6 is connected to an endotracheal tube 48 which has an opening 50 for gas communication with a patient's airways. A small bore tube 52, which may be formed integrally with the endotracheal tube 48, is also provided and has an open end 52 which preferably terminates within the endotracheal tube 48 and is connected at its opposite end to an inlet 56 of a size variable gas holding volume 58 of an extraction device 60.

The extraction device 60 has a magnetically movable diaphragm 62 which forms a movable wall section of the gas holding volume 58. Electromagnetic drive units 64 are provided to reciprocate the diaphragm 62 in response to an AC signal from a signal generator 28 which is supplied in synchronism with a control signal also supplied by the generator 28 and used to control the operation of the oscillator 16. In this manner the size of the gas holding volume 58 can be varied in timed relation with the phases of the breathing cycles generated by the oscillator 16, preferably to extract gas from the patient's airways during expiration phases. In use, as the diaphragm 62 moves to increase the size of the volume 58 $CO_2$ rich breathing gas will be drawn into the volume 58 through the inlet 56 from the small bore tube 52. As the diaphragm moves to decrease the size of the volume 58 the $CO_2$ rich gas will be expelled from the extraction device through an outlet 66. One-way valves 68, 70 are respectively disposed in gas communication with the inlet 56 and the outlet 66 and are arranged to ensure that gas can pass through the extraction device 60 in one direction only, that is from inlet 56 to outlet 66, as the diaphragm 62 reciprocates. It will be appreciated by those skilled in the art that the diaphragm 62 may be driven by conventional means other than electromagnetic drive units 64 and that the diaphragm 62 may be replaced by other conventional reciprocating elements, such as a piston, without departing from the scope of the invention.

A bias gas flow is provided by a gas supply 32 to an inlet 34 sited at the Y-piece 6 and passes out of the ventilator 46 through the limb 10. The gas supply is provided with a flow regulator 72 to control the flow of bias gas to the inlet 34. The flow regulator 72 comprises a variable opening valve which increases its opening by a predetermined amount as the extraction device 60 operates to withdraw gas from the respiration flow-path and decreases its opening by the same predetermined amount when gas is no longer withdrawn from the respiration flow-path. The opening and closing of the valve of the flow regulator 72 is synchronized with the operation of the extraction device 60 of a control signal received from the signal generator 28.

Figure 3:
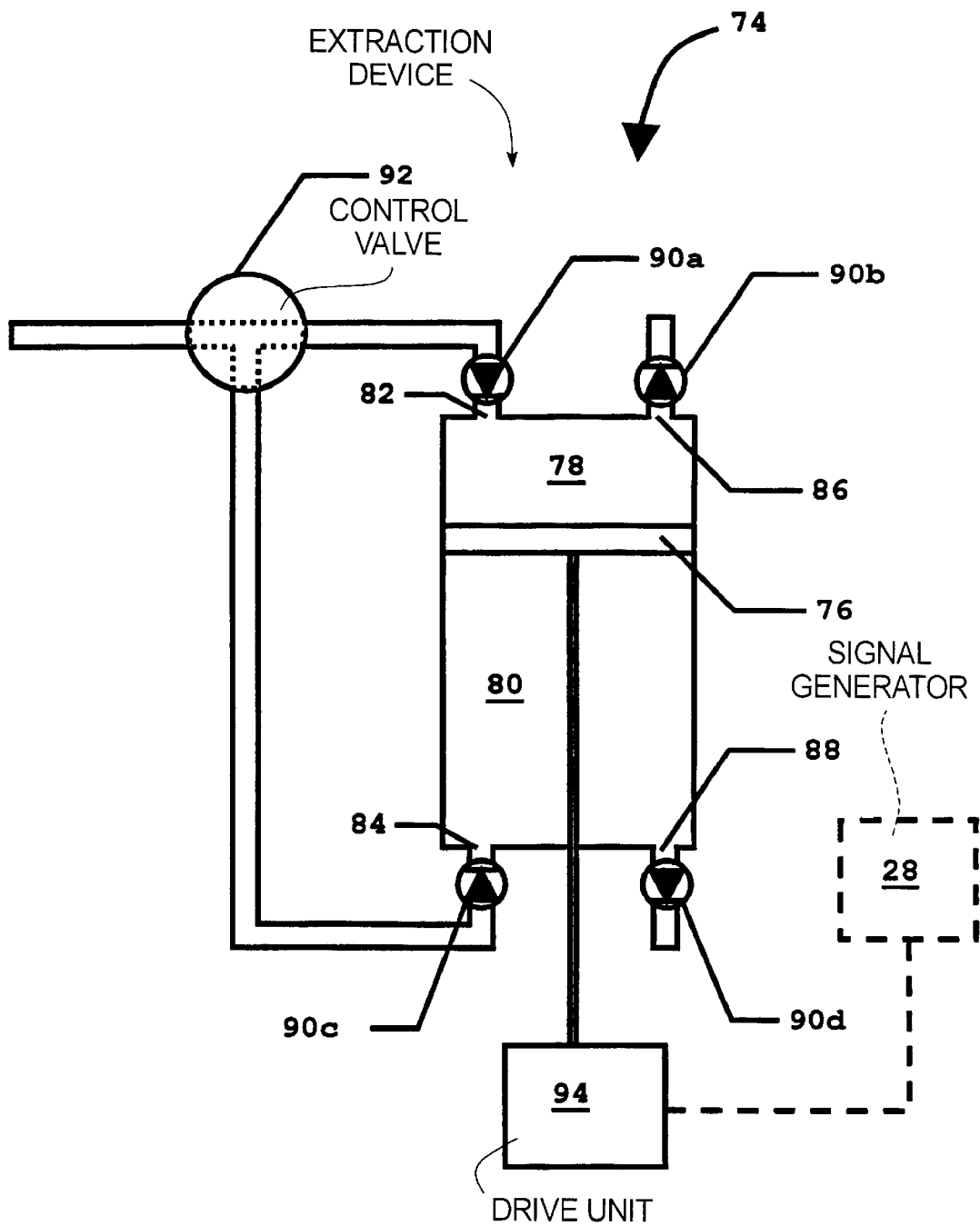
FIG. 3 is a schematic representation of a further extraction device for use as part of an HFO ventilator according to the present invention.

A further extraction device 74 is shown in FIG. 3 and may be used to replace those extraction devices 38, 44 and 60 illustrated in FIG. 1 and FIG. 2, respectively. A reciprocally movable element, here shown as a piston head 76, is arranged as a dividing wall between two size-variable gas holding volumes 78, 80 which are caused to vary counter to one another by the reciprocation of the piston 76. Each volume 78, 80 is provided with a gas inlet 82, 84 and a gas outlet 86, 88 connected in gas communication with individual one-way valves 90a, 90b, 90c and 90d which are disposed to ensure that gas flows into and out of each of the volumes 78, 80 in one direction only. A control valve 92, which may be a 'T'-valve, provides a selectable connection of one or both inlets 82, 84 to the respiration flow-path.

A drive unit 94 of the extraction device 74 is operable to reciprocate the piston head 76 in timed relation to the operation of an oscillator used to induce high-frequency pressure oscillations along a respiration flow-path of an HFO ventilator (not shown) of which the extraction device 74 is a component. To this end a signal generator 28 which also supplies the high-frequency control signal for the oscillator, for example as described with respect to the HFO ventilator 2 of FIG. 1, is operably connected to the drive unit 94 to supply a control signal thereto at a frequency dependent on that of the signal supplied to the oscillator, and which is used by the unit 94 to control the reciprocation frequency of the piston 76.

As an example, the operation of the extraction device 72 will now be described for the situation where the valve 90 is set to connect both inlets 80, 82 to the respiration flow-path. As the piston head moves to reduce the size of the volume 80 gas within that volume is forced out of the outlet 88. Simultaneously, the size of the volume 78 increases and gas from the respiration flow-path enters the volume 78 via the inlet 82.

At the end of the piston stroke the piston head is driven in the opposite direction by the unit 92 to reduce the size of the volume 78 and thereby expelling gas through the outlet 86. Simultaneously the size of the volume 80 increases and gas enters through the inlet 84. The extraction device 74 can be adapted to operate to extract breathing gas during the whole or part of a breathing cycle of an HFO ventilator through selection of the reciprocation frequency and the maximum size of the volumes 80, 78 as well as by choice of operating position of the control valve 92.

Although modifications and changes may be suggested by those skilled in the art, it is the intention of the inventor to embody within the patent warranted hereon all changes and modifications as reasonably and properly come within the scope of his contribution to the art.

I claim as my invention:

1. A high-frequency oscillator ventilator comprising:
    a gas conduit having an opening adapted for gaseous connection with airways of a patient, and having a bias gas flow inlet, adapted for connection to a source of bias gas, and a bias gas flow outlet disposed relative to said bias gas flow inlet to define a bias gas flow path within said gas conduit in which a bias gas flow flows, causing removal of an amount of gas from said gas conduit;
    an oscillator operably connected to said conduit for generating alternating overpressure and underpressure pulses to induce pressure oscillations in gas within said conduit and move a volume of gas along a respiration flow path, intersecting said bias gas flow path, in alternation into and out of said opening at a predetermined high-frequency, thereby producing an inspiration phase and an expiration phase of a breathing cycle; and
    an extraction device operably connected to said conduit during said breathing cycle to withdraw gas from said respiration flow path in a timed relationship with said pressure oscillations and in addition to said amount of gas removal by said bias gas flow.

2. A high-frequency oscillator ventilator as claimed in claim 1 wherein said extraction device is coupled in gaseous communication to said respiration flow path at a location beyond said bias gas flow path in a direction toward said opening.

3. A high-frequency oscillator ventilator as claimed in claim 1 wherein said extraction device withdraws gas only during a portion of said breathing cycle predominantly comprising said expiration phase, and further comprising a flow controller in gaseous communication with said bias gas flow inlet for varying a flow of bias gas through said bias gas flow inlet dependent on operation of said extraction device.

4. A high-frequency oscillator ventilator as claimed in claim 3 wherein said extraction device withdraws gas only within said expiration phase.

5. A high-frequency oscillator ventilator as claimed in claim 3 wherein said flow controller is a pressure regulator which varies said bias flow to maintain a predetermined mean airway pressure within said conduit.

6. A high-frequency oscillator ventilator as claimed in claim 1 wherein said extraction device has a size-variable gas holding volume in gaseous communication with said respiration flow path, and wherein said extraction device alternately increases a size of said volume to withdraw gas from said respiratory flow path and decreases the size of the volume to vent withdrawn gas away from said respiratory flow path.

7. A high-frequency oscillator ventilator as claimed in claim 1 wherein said extraction device is a vacuum pump coupled in gaseous communication with said respiration flow path.

* * * * *